United States Patent
Siefker

(10) Patent No.: US 10,586,645 B2
(45) Date of Patent: Mar. 10, 2020

(54) TRANSFORMER SYSTEMS AND METHODS FOR OPERATING A TRANSFORMER SYSTEM

(71) Applicant: ABB Schweiz AG, Baden (CH)

(72) Inventor: Bryan Siefker, Maryland Heights, MO (US)

(73) Assignee: ABB Power Grids Switzerland AG, Baden (CH)

( * ) Notice: Subject to any disclaimer, the term of this patent is extended or adjusted under 35 U.S.C. 154(b) by 0 days.

(21) Appl. No.: 15/676,568

(22) Filed: Aug. 14, 2017

(65) Prior Publication Data
US 2019/0051443 A1  Feb. 14, 2019

(51) Int. Cl.
| | |
|---|---|
| *H01F 27/10* | (2006.01) |
| *H01F 27/12* | (2006.01) |
| *G01N 29/04* | (2006.01) |
| *G01M 3/02* | (2006.01) |
| *G01F 23/30* | (2006.01) |
| *G01M 3/32* | (2006.01) |
| *H01F 27/40* | (2006.01) |

(52) U.S. Cl.
CPC .......... *H01F 27/12* (2013.01); *G01F 23/30* (2013.01); *G01M 3/02* (2013.01); *G01M 3/3227* (2013.01); *G01M 3/3245* (2013.01); *G01N 29/04* (2013.01); *H01F 27/402* (2013.01)

(58) Field of Classification Search
CPC ........ H01F 27/12; H01F 27/14; H01F 27/125; H01F 27/105; H01F 27/10; H01F 27/16; H01F 27/18; G01N 29/04; G01M 3/02; G01F 23/30
USPC .......................... 336/57, 58, 90, 94
See application file for complete search history.

(56) References Cited

U.S. PATENT DOCUMENTS

| | | | | |
|---|---|---|---|---|
| 4,581,477 A | * | 4/1986 | Harumoto | H01F 27/18 165/104.27 |
| 4,607,245 A | * | 8/1986 | Kuroda | H01F 27/18 174/11 R |
| 5,415,033 A | * | 5/1995 | Maresca, Jr. | G01M 3/2807 73/40.5 R |
| 6,401,518 B1 | * | 6/2002 | O'Keeffe | H01F 27/12 73/19.01 |
| 6,909,349 B1 | * | 6/2005 | Longardner | F25B 15/00 336/60 |
| 7,636,233 B2 | | 12/2009 | Callsen et al. | |
| 8,461,953 B1 | * | 6/2013 | Ward | H01F 27/08 336/55 |

(Continued)

FOREIGN PATENT DOCUMENTS

WO     2016065143 A2   4/2016

*Primary Examiner* — Mang Tin Bik Lian
(74) *Attorney, Agent, or Firm* — Taft Stettinius & Hollister LLP

(57) ABSTRACT

A transformer system includes a transformer and a transformer tank housing the transformer in a bath of a coolant; and a plurality of radiator systems operative to transfer heat from the coolant, each radiator system being in fluid communication with the transformer tank. The transformer system also includes means for determining an occurrence of a potential coolant leak in one or more radiator system of the plurality of radiator systems; and means for isolating only radiator systems of the plurality of radiator systems that are leaking, in response to a determination of the occurrence of the potential coolant leak.

19 Claims, 3 Drawing Sheets

(56) References Cited

U.S. PATENT DOCUMENTS

| | | | |
|---|---|---|---|
| 2007/0001793 A1* | 1/2007 | Magnier | H01F 27/402 336/90 |
| 2009/0000763 A1 | 1/2009 | Bercea et al. | |
| 2009/0180514 A1 | 7/2009 | Anderson | |
| 2009/0315657 A1 | 12/2009 | Hoffman et al. | |
| 2011/0140820 A1* | 6/2011 | Guentert, III | H01F 27/12 336/58 |
| 2016/0118186 A1* | 4/2016 | Frimpong | G01H 1/00 307/119 |

* cited by examiner

TRANSFORMER SYSTEMS AND METHODS FOR OPERATING A TRANSFORMER SYSTEM

TECHNICAL FIELD

The present application generally relates to electrical systems, and more particularly, but not exclusively, to transformer systems and methods for operating a transformer system.

BACKGROUND

Transformer systems of various types, e.g., high power high voltage (HV) transformer systems, remain an area of interest. Some existing systems have various shortcomings, drawbacks and disadvantages relative to certain applications. For example, in some transformer systems, a radiator leak may result in damage to the transformer. Accordingly, there remains a need for further contributions in this area of technology.

SUMMARY

One embodiment of the present invention is a unique transformer system. Another embodiment is unique method for operating a transformer system. Another embodiment is a unique transformer system. Other embodiments include apparatuses, systems, devices, hardware, methods, and combinations for transformer systems. Further embodiments, forms, features, aspects, benefits, and advantages of the present application shall become apparent from the description and figures provided herewith.

BRIEF DESCRIPTION OF THE FIGURES

The description herein makes reference to the accompanying drawings wherein like reference numerals refer to like parts throughout the several views, and wherein.

DETAILED DESCRIPTION OF THE ILLUSTRATIVE EMBODIMENTS

Figure 1:
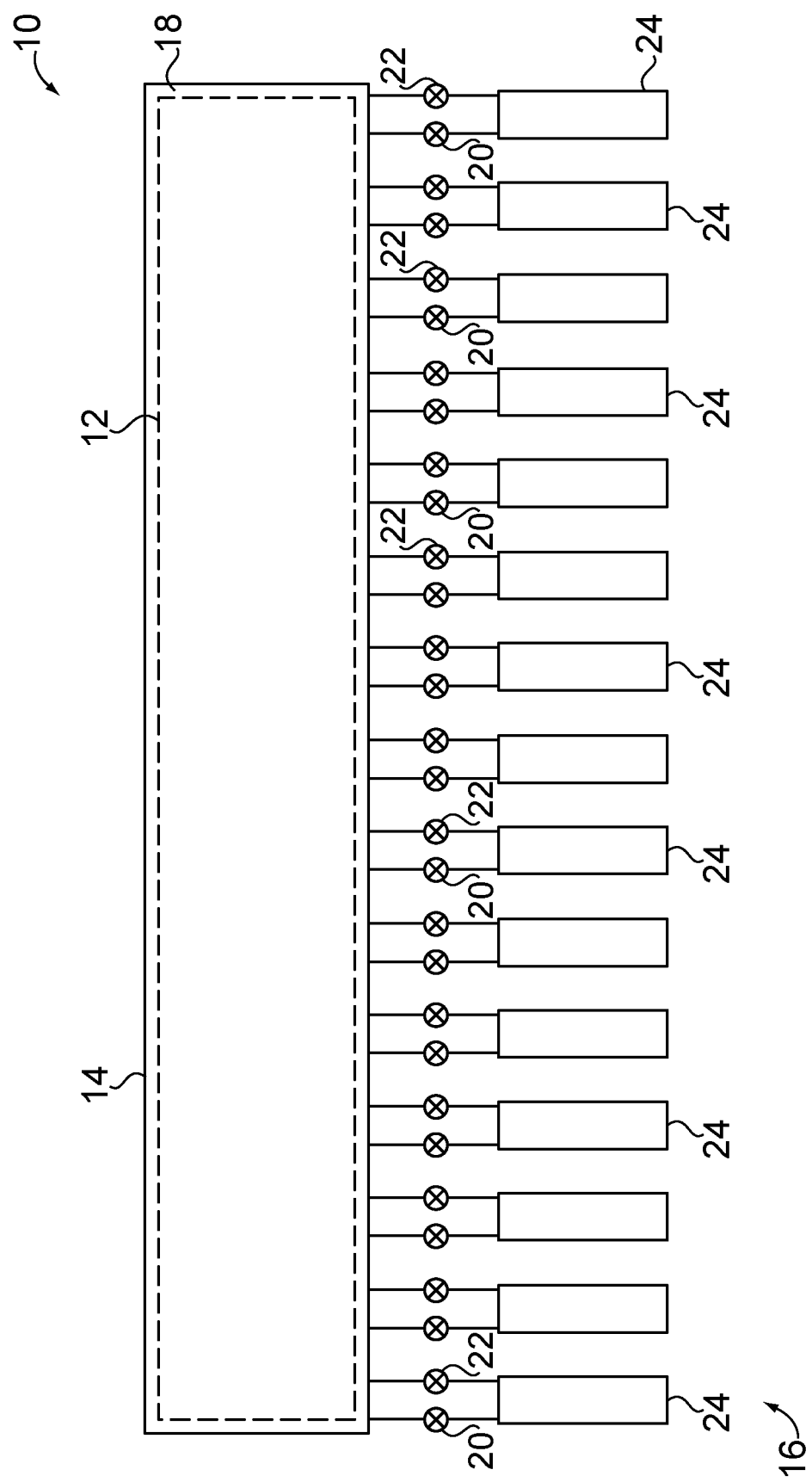
FIG. 1 schematically illustrates a plan view of some aspects of a non-limiting example of a transformer system in accordance with an embodiment of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Figure 2:
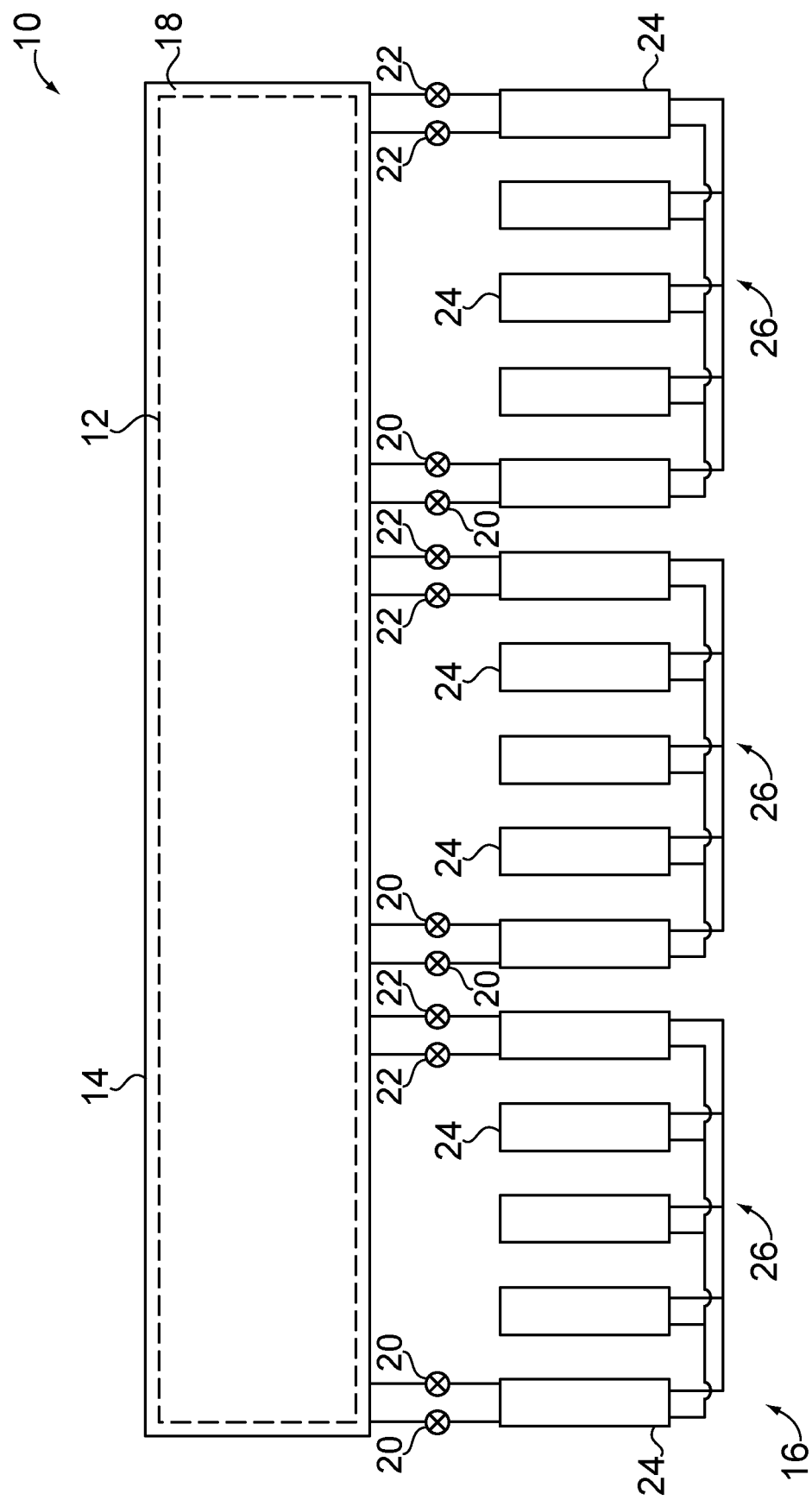
FIG. 2 schematically illustrates a plan view of some aspects of a non-limiting example of a transformer system in accordance with an embodiment of the present invention.

Referring to FIG. 1, a plan view of some aspects of a non-limiting example of a transformer system 10 in accordance with an embodiment of the present invention is schematically illustrated. Transformer system 10 includes a transformer 12, a transformer tank 14 and a plurality of radiators systems 16. In one form, transformer 12 is a HV transformer. In other embodiments, transformer 12 may be a medium voltage (MV) or low voltage (LV) transformer. Transformer 12 is housed within tank 14 in a bath of coolant 18, e.g., a dielectric fluid, such as a dielectric oil or SF6. Radiator systems 16 are operative to transfer heat from coolant 18. Each radiator system 16 includes at least one top actuated valve 20 (e.g., electronically actuated) and at least one bottom actuated valve 22 (e.g., electronically actuated). Top actuated valve 20 and bottom actuated valve 22 are actuatable valves operative to open or close to respectively expose or isolate a radiator system 16 from tank 14, e.g., under the direction of a controller, e.g., as described below. In some embodiments, one or more radiator systems 16 are each an individual radiator 24 fluidly coupled to tank 14 via valves 20, 22, e.g., as depicted in FIG. 1. Referring also to FIG. 2, in some embodiments, one or more radiator systems 16 may be a bank 26 of individual radiators 24, e.g., coupled in parallel to each other as depicted in FIG. 2, or in some embodiments one or more banks 26 may also or alternatively be a plurality of individual radiators 24 coupled in series. Whereas FIG. 1 depicts radiator systems 16 in the form of fifteen individual radiators 24, and FIG. 2 depicts radiator systems 16 in the form of three (3) banks of five (5) individual radiators 24, it will be understood that in various embodiments, some radiator systems 16 may be individual radiators 24, and others may be organized into banks 26, including in the same embodiment. The number of radiators 24, and the number of banks 26, as well the number of radiators 24 within each bank may vary with the needs of the application. Top actuated valves 20 fluidly couple the top of radiator systems 16, e.g., banks 26 of radiators 24 or individual radiators 24, to a top or upper portion of tank 14, whereas bottom actuated valves 22 fluidly couple the bottom of radiator systems 16, e.g., banks 26 of radiators 24 or individual radiators 24, to bottom or lower portion of tank 14. When organized into banks, a lesser number of top actuated valves 20 and bottom actuated valves 22 per radiator may be employed, e.g., less than one of each valve per radiator 24 in a given bank. For example, whereas in FIG. 1, each individual radiator 24 includes a top actuated valve and a bottom actuated valve, in the embodiment of FIG. 2, each bank 26 of five (5) radiators 24 employs two (2) top actuated valves 20 and two bottom actuated valves 22. The number of top actuated valves 20 and the number of bottom actuated valves 22 per bank 26 or per individual radiator 24 may vary with the needs of the application. In one form, radiator systems 16 employ natural convection. In other embodiments, forced flow cooling may be employed.

Figure 3:
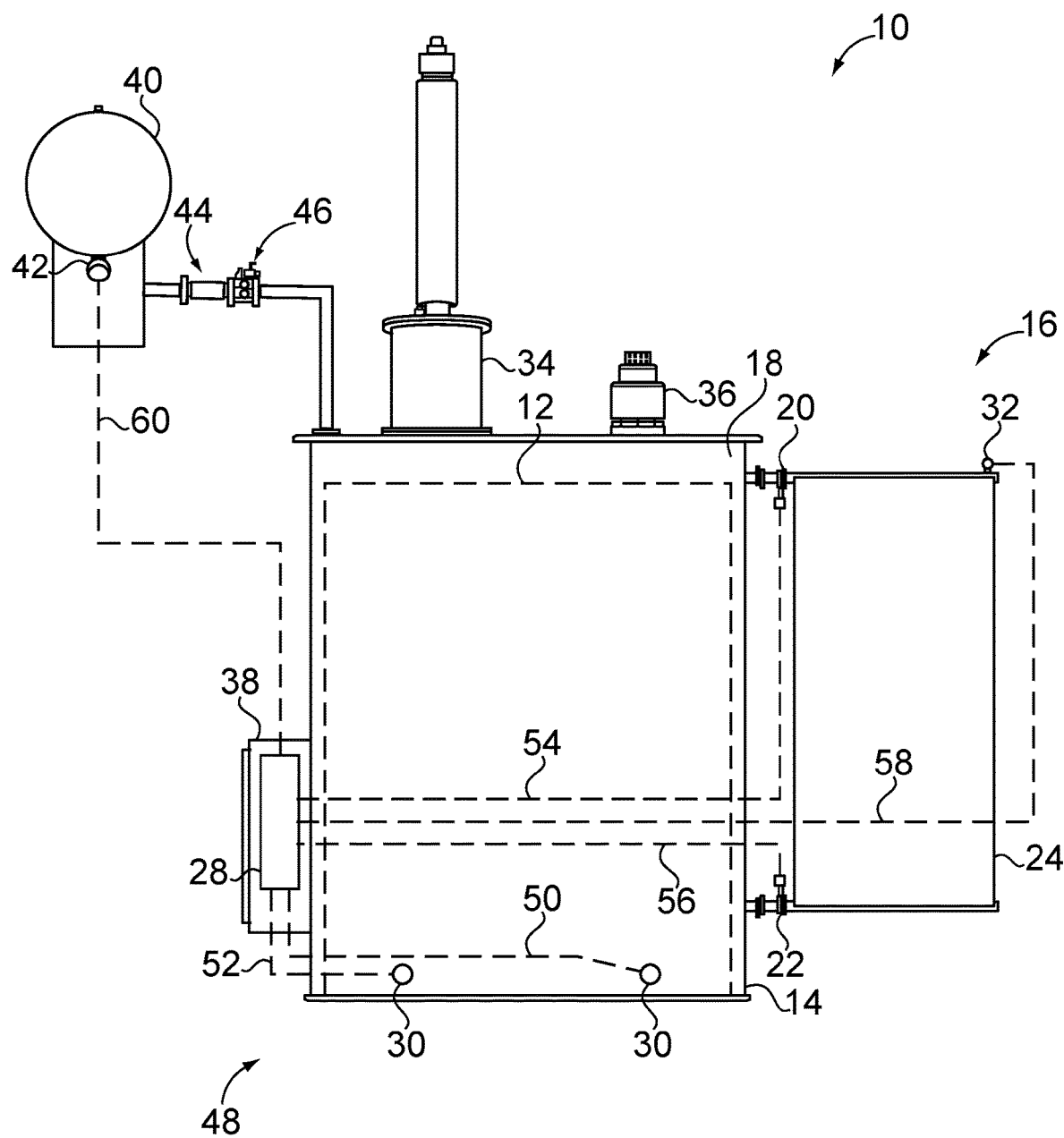
FIG. 3 schematically illustrates a side view of some aspects of a non-limiting example of transformer system in accordance with an embodiment of the present invention.

Referring to FIG. 3, a side view of some aspects of a non-limiting example of transformer system 10 in accordance with an embodiment of the present invention is schematically illustrated. Transformer system 10 also includes a controller 28, a plurality of ballistic impact sensors 30, e.g., one or more such ballistic impact sensors being located on tank 14, e.g., on each side of tank 14 (two of which are illustrated in the side view of FIG. 3; it will be understood that in some embodiments, ballistic impact sensors may be located on other portions or components of transformer system 10); a float level sensor or switch 32 for each radiator system 16; a plurality of hardened turrets 34 and 36; a hardened control cabinet 38, e.g., housing controller 28; a hardened conservator 40 having a low coolant level indicator 42; a shutter valve 44; and a Buchholz relay 46. It will be understood that the term, "ballistic impact" includes impacts by bullets or other projectiles fired by weapons, e.g., rifles, shotguns or handguns, and in some embodiments includes impacts by other objects, e.g., objects thrown by a human, impacts due to hand-held objects being used to strike tank 14 or another transformer system 10 component, or objects sent on a ballistic trajectory to strike tank 14 or another transformer system 10 component by other means. Tank 14 is hardened. The term, "hardened," as used herein, refers to hardening against ballistic damage, e.g., against a ballistic bullet impact and/or preventing a loss of coolant after a ballistic impact. Hardening may be achieved, for example, as set forth in International Publication No. WO 2016/065143 A2, which is incorporated herein by reference. For example, tank 14, control cabinet 38 and conservator 40 may be constructed of ½" AR500 armor steel with a ½" polyurea coating configured to meet UL Standard 752, Level 10 ballistic rating. In the illustrated embodiment, radiator systems 16 are not hardened, although they may be hardened in other embodiments.

Controller 28 and ballistic impact sensors 30 form a ballistic impact detection system 48. A ballistic impact detection system using ballistic impact sensors, e.g., acoustic and vibration sensors, is described in International Publication No. WO 2016/065143 A2, which, as set forth above, is incorporated herein by reference.

Ballistic impact sensors 30 are operative to sense a ballistic impact, e.g., on the walls of tank 14. Ballistic impact sensors 30 are communicatively coupled to controller 28 via communication links 50 and 52. Each top actuated valve 20 is communicatively coupled to controller 28 via communications links 54. Each bottom actuated valve 22 is communicatively coupled to controller 28 via communications links 56. Each float level sensor 32 is communicatively coupled to controller 28 via communications links 58. Float level sensors 32 may be installed, for example, at the vent plug of each radiator system 16, e.g., one for individual radiators 24 coupled to tank 14, and one or more for each bank 26 of radiators coupled to tank 24. Float level sensors 32 are operative to detect the level of coolant in each radiator system 16, e.g., each individual radiator 24 or each bank 26 of radiators. Low coolant level indicator 42 is communicatively coupled to controller 28 via communications link 60. In one form, communication links 50, 52, 54, 56, 58 and 60 are wired links. In other embodiments, one or more of communication links 50, 52, 54, 56, 58 and 60 may be wireless or optical communication links.

Ballistic impact detection system 48 is operative to determine an occurrence of a potential coolant leak in one or more radiator system 16 of the plurality of radiator systems. For example, ballistic impact detection system 48 is operative to determine an occurrence of a ballistic impact on the transformer system 10, e.g., on transformer tank 14, based on the output of ballistic impact sensors 30. Being protected against ballistic impact, transformer tank 14 may not leak coolant. However, a ballistic impact on transformer tank 14 may also mean that one or more radiator systems 16 have been damaged, e.g., either by shrapnel or a ricochet from tank 14 or another structure, or by direct weapons fire against radiators 16. For example, a ballistic impact on transformer tank 14 or other ballistic event detection based on ballistic impact sensors 30 may indicate an active shooter and that ballistic impacts may have occurred elsewhere on transformer system 10, such as one or more of radiator systems 16 and/or associated piping or other associated hardware. Upon a determination of the occurrence of the ballistic impact, e.g., on tank 14, controller 28 is operative to direct each top actuated valve 20 and each bottom actuated valve 22 to close, thereby isolating all radiator systems 16 from transformer tank 14. By isolating radiator systems 16 from transformer tank 14, potentially damaged radiator systems 16, e.g., radiator systems 16 that have received a direct ballistic impact, ricochet or shrapnel impact and may thus be leaking, are prevented from allowing the coolant in tank 14 to leak out through the damaged radiator.

After a ballistic impact has been determined, top actuated valves 20 and bottom actuated valves 22 are closed. Controller 28 is then operative wait a predetermined period of time, e.g., one minute or some other suitable time period, and to then read the output of the float level sensors 32. Controller 28 then determines which radiator systems 16, if any, are leaking, e.g., based upon which float sensors have tripped, indicating a drop in oil level. Those radiator systems 16 having no change in coolant level are deemed to be not leaking, whereas those having a change in coolant level are deemed to be leaking. After having determined which radiator systems 16 are leaking, if any, controller 28 directs the top actuated valves 20 and bottom actuated valves 22 to reopen, for only those radiator systems 16 that are not leaking, thus allowing continued cooling of transformer 12, and ultimately isolating from transformer tank 14 only those radiator systems 16 that are leaking.

Conservator 40 low coolant level indicator 42, along with controller 28 is operative to determine an occurrence of a potential coolant leak in one or more radiator system of the plurality of radiator systems. Conservator 40 is in fluid communication with transformer tank 14, e.g., via shutter valve 44 and Buchholz relay 46. Controller 28 is operative to determine if a coolant loss has occurred based on an output of low coolant level indicator 42. If low coolant level indicator 42 of conservator 40 indicates to controller 28 that the coolant 18 level is low, this may be an indication of a leak in one or more of the radiator systems 16, e.g., due to a ballistics event or other cause. In some cases, a low coolant level indication from low coolant level indicator 42 may indicate other problems. In any event, in some embodiments, controller 28 shuts transformer 12 down to prevent damage in the event of a low coolant level indication from low coolant level indicator 42.

In other embodiments, if controller 28 determines the coolant 18 level is low or that a loss of coolant 18 has occurred, controller 28 is operative to direct each top actuated valve 20 and each bottom actuated valve 22 to close, thereby isolating all radiator systems 16 from transformer tank 14. After a low coolant level in conservator 40 has been determined, based on the output of low coolant level indicator 42, controller 28 determines whether any of the radiator systems are leaking, based on the output of float level sensors 32. Controller 28 is then operative wait a predetermined period of time, e.g., one minute or some other suitable time period, and to then read the output of the float level sensors 32. Controller 28 then determines which radiator systems 16, if any, are leaking, e.g., based upon which float sensors have tripped, indicating a drop in oil level. Those radiators having no change in coolant level are deemed to be not leaking, whereas those having a change in coolant level are deemed to be leaking. After having determined which radiator systems 16 are leaking, if any, controller 28 directs the top actuated valves 20 and bottom actuated valves 22 to reopen, only for those radiator systems 16 that are not leaking, thus allowing continued cooling of transformer 12, and ultimately isolating from transformer tank 14 only those radiator systems 16 that are leaking.

Embodiments of the present invention include a transformer system, comprising: a transformer; a transformer tank housing the transformer in a bath of a coolant; a ballistic impact detection system having a controller and at least one ballistic impact sensor communicatively coupled to the controller, wherein the ballistic impact detection system is operative to determine an occurrence of a ballistic impact on the transformer system based on an output of the at least one ballistic impact sensor; and a plurality of radiator systems operative to transfer heat from the coolant, each radiator system of the plurality of radiator systems having a top actuated valve communicatively coupled to the controller and fluidly coupling the top of the each radiator system to the transformer tank; and a bottom actuated valve communicatively coupled to the controller and fluidly coupling the bottom of the each radiator system to the transformer tank, wherein upon a determination of the occurrence of the ballistic impact, the controller is operative to direct each top actuated valve and each bottom actuated valve to close.

In a refinement, each radiator system includes a float level sensor communicatively coupled to the controller and operative to detect a level of the coolant in each radiator system of the plurality of radiator systems; and the controller is operative to determine whether any of the radiator systems of the plurality of radiator systems are leaking coolant based on an output of the float level sensors.

In another refinement, the controller is operative to: wait a predetermined period of time after determining the occurrence of a ballistic impact; read the output of the float level sensors after waiting the predetermined period of time; and determine which radiator systems of the plurality of radiator systems are leaking based upon the read output of the float level sensors.

In yet another refinement, the controller is operative to direct the top actuated valve and the bottom actuated valve to reopen, only for those radiator systems of the plurality of radiator systems that are not determined to be leaking.

In still another refinement, the transformer system further comprises a conservator in fluid communication with the transformer tank; wherein the conservator includes a low coolant level indicator; wherein the controller is operative to determine if a coolant loss has occurred based on an output of the low coolant level indicator; and wherein upon a determination that the coolant loss has occurred, the controller is operative to direct each top actuated valve and each bottom actuated valve to close.

In yet still another refinement, each radiator system of the plurality of radiator systems includes a float level sensor communicatively coupled to the controller and operative to detect a level of the coolant in the each radiator system; and the controller is operative to determine whether any of the radiator systems are leaking coolant based on the output of the float level sensors.

In a further refinement, the controller is operative to: wait a predetermined period of time after determining that the coolant loss has occurred based on the output of the low coolant level indicator, read the output of the float level sensors; and determine which radiator systems are leaking based upon the read output of the float level sensors.

In a yet further refinement, the controller is operative to direct the top actuated valve and the bottom actuated valve to reopen, only for those radiator systems of the plurality of radiator systems that are not determined to be leaking.

Embodiments of the present invention include a method for operating a transformer system, comprising: housing a transformer in a bath of a coolant in a transformer tank; transferring heat from the coolant using a plurality of radiator systems in fluid communication with the transformer tank via a plurality of actuated valves; detecting a ballistic impact on the transformer system; isolating the plurality of radiator systems from the transformer tank by closing the plurality of actuated valves in response to the detecting of the ballistic impact.

In a refinement, the method further comprises determining whether any radiator systems of the plurality of radiator systems are leaking coolant.

In another refinement, each radiator system of the plurality of radiator systems includes a float level sensor; and the determination of whether any of the radiator systems of the plurality of radiator systems are leaking coolant is made based on an output of the float level sensors.

In yet another refinement, the method further comprises waiting a predetermined period of time after detecting the ballistic impact; reading the output of the float level sensors after waiting the predetermined period of time; and determining which radiator systems are leaking based upon the reading of the output of the float level sensors.

In still another refinement, the method further comprises reopening only the actuated valves for those radiator systems of the plurality of radiator systems that are not determined to be leaking.

In yet still another refinement, the transformer includes a conservator in fluid communication with the transformer tank; wherein the conservator includes a low coolant level indicator, further comprising determining if a coolant loss has occurred based on an output of the low coolant level indicator; and isolating the plurality of radiator systems from the transformer tank by closing the actuated valves in response to determining that the coolant loss has occurred.

In a further refinement, each radiator system includes a float level sensor operative to detect a level of the coolant in the each radiator system; further comprising determining whether any of the radiator systems are leaking coolant based on an output of the float level sensors.

In a yet further refinement, the method further comprises waiting a predetermined period of time after determining that the coolant loss has occurred based on the output of the low coolant level indicator; reading the output of the float level sensors after waiting the predetermined period of time; and determining which radiator systems are leaking coolant based upon the reading of the output of the float level sensors.

In a still further refinement, the method further comprises reopening the actuated valves of the plurality of actuated valves only for those radiator systems of the plurality of radiator systems that are not determined to be leaking.

Embodiments of the present invention include a transformer system, comprising: a transformer; a transformer tank housing the transformer in a bath of a coolant; a plurality of radiator systems operative to transfer heat from the coolant, each radiator system being in fluid communication with the transformer tank; means for determining an occurrence of a potential coolant leak in one or more radiator system of the plurality of radiator systems; and means for isolating only radiator systems of the plurality of radiator systems that are leaking, in response to a determination of the occurrence of the potential coolant leak.

In a refinement, the means for determining the occurrence of the potential coolant leak includes a ballistic impact detection system having a controller and a ballistic impact sensor communicatively coupled to the controller, wherein the ballistic impact detection system is operative to determine an occurrence of a ballistic impact on the transformer system based on the output of the ballistic impact sensor.

In another refinement, the means for determining the occurrence of the potential coolant leak includes a controller, and a conservator having a low coolant level indicator coupled to the controller and operative to indicate a low level of the coolant.

While the invention has been illustrated and described in detail in the drawings and foregoing description, the same is to be considered as illustrative and not restrictive in character, it being understood that only the preferred embodiments have been shown and described and that all changes and modifications that come within the spirit of the inventions are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

What is claimed is:

1. A transformer system, comprising:
   a transformer;
   a transformer tank housing the transformer in a bath of a coolant;
   a ballistic impact detection system having a controller and at least one ballistic impact sensor communicatively coupled to the controller, wherein the ballistic impact detection system is operative to determine an occurrence of a ballistic impact on the transformer system based on an output of the at least one ballistic impact sensor; and
   a plurality of radiator systems operative to transfer heat from the coolant, each radiator system of the plurality of radiator systems having a top actuated valve communicatively coupled to the controller and fluidly coupling the top of the each radiator system to the transformer tank; a bottom actuated valve communicatively coupled to the controller and fluidly coupling the bottom of the each radiator system to the transformer tank; and a float level sensor communicatively coupled to the controller and operative to detect a level of the coolant in each radiator system of the plurality of radiator systems;
   wherein upon a determination of the occurrence of the ballistic impact, the controller is operative to direct each top actuated valve and each bottom actuated valve to close, and
   wherein the controller is operative to determine, after each top actuated valve and each bottom actuated valve are closed, whether any of the radiator systems of the plurality of radiator systems are leaking coolant based on an output of the float level sensors.

2. The transformer system of claim 1, wherein the controller is operative to, after a predetermined period of time after each top actuated valve and each bottom actuated valve are closed, read the output of the float level sensors.

3. The transformer system of claim 2, wherein the controller is operative to, after the predetermined period of time, determine based on the output of the float level sensors which radiator systems of the plurality of radiator systems are leaking based upon the read output of the float level sensors.

4. The transformer system of claim 3, wherein the controller is operative to direct the top actuated valve and the bottom actuated valve to reopen, only for those radiator systems of the plurality of radiator systems that are not determined to be leaking.

5. The transformer system of claim 1, further comprising a conservator in fluid communication with the transformer tank; wherein the conservator includes a low coolant level indicator; wherein the controller is operative to determine if a coolant loss has occurred based on an output of the low coolant level indicator; and wherein upon a determination that the coolant loss has occurred, the controller is operative to direct each top actuated valve and each bottom actuated valve to close.

6. The transformer system of claim 5, wherein the controller is operative to: wait a predetermined period of time after determining that the coolant loss has occurred based on the output of the low coolant level indicator, read the output of the float level sensors; and determine which radiator systems are leaking based upon the read output of the float level sensors.

7. The transformer system of claim 6, wherein the controller is operative to direct the top actuated valve and the bottom actuated valve to reopen, only for those radiator systems of the plurality of radiator systems that are not determined to be leaking.

8. A method for operating a transformer system, comprising:
   housing a transformer in a bath of a coolant in a transformer tank;
   transferring heat from the coolant using a plurality of radiator systems in fluid communication with the transformer tank via a plurality of actuated valves;
   detecting a ballistic impact on the transformer system;
   isolating the plurality of radiator systems from the transformer tank by closing the plurality of actuated valves in response to the detecting of the ballistic impact; and
   reading, after closing the plurality of actuated valves, an output of a float level sensor of each radiator system of the plurality of radiator systems.

9. The method of claim 8, further comprising determining whether any radiator systems of the plurality of radiator systems are leaking coolant.

10. The method of claim 9, wherein the determination of whether any of the radiator systems of the plurality of radiator systems are leaking coolant is made based on the output of the float level sensor of each radiator system of the plurality of radiator systems.

11. The method of claim 10, further comprising reading the output of the float level sensors after a predetermined period of time; and determining which radiator systems are leaking based upon the reading of the output of the float level sensors.

12. The method of claim 11, further comprising reopening only the actuated valves for those radiator systems of the plurality of radiator systems that are not determined to be leaking.

13. The method of claim 8, wherein the transformer includes a conservator in fluid communication with the transformer tank; wherein the conservator includes a low coolant level indicator, further comprising determining if a coolant loss has occurred based on an output of the low coolant level indicator; and isolating the plurality of radiator systems from the transformer tank by closing the actuated valves in response to determining that the coolant loss has occurred.

14. The method of claim 13, further comprising determining whether any of the radiator systems are leaking coolant based on the output of the float level sensors.

15. The method of claim 14, further comprising waiting a predetermined period of time after determining that the coolant loss has occurred based on the output of the low coolant level indicator; reading the output of the float level sensors after waiting the predetermined period of time; and determining which radiator systems are leaking coolant based upon the reading of the output of the float level sensors.

16. The method of claim 15, further comprising reopening the actuated valves of the plurality of actuated valves only for those radiator systems of the plurality of radiator systems that are not determined to be leaking.

17. A transformer system, comprising:
a transformer;
a transformer tank housing the transformer in a bath of a coolant;
a plurality of radiator systems operative to transfer heat from the coolant, each radiator system being in fluid communication with the transformer tank, each radiator system of the plurality of radiator systems including a plurality of valves and a float level sensor, the plurality of valves positioned to selectively isolate the radiator system from the transformer, the float level sensor positioned to detect a level of the coolant in the radiator system; and
a controller in communication with the float level sensor of each radiator system of the plurality of radiator systems, the controller configured to determine, from an output of the float level sensor representative of the level of coolant in the radiator system after the plurality of valves are closed, the absence and/or presence of a leakage of the coolant for each of the plurality of radiator systems.

18. The transformer system of claim 17, further including a ballistic impact detection system having a ballistic impact sensor communicatively coupled to the controller, wherein the ballistic impact detection system is operative to determine an occurrence of a ballistic impact on the transformer system based on the output of the ballistic impact sensor.

19. The transformer system of claim 18, further including a conservator having a low coolant level indicator coupled to the controller and operative to indicate a low level of the coolant.

* * * * *